United States Patent
Brodkin (10) Patent No.: US 7,279,238 B2
(45) Date of Patent: Oct. 9, 2007

(54) PRESSABLE GLASS-CERAMICS WITH TEXTURED MICROSTRUCTURE

(75) Inventor: Dmitri Brodkin, Livingston, NJ (US)

(73) Assignee: Pentron Ceramics, Inc., Somerset, NJ (US)

( * ) Notice: Subject to any disclaimer, the term of this patent is extended or adjusted under 35 U.S.C. 154(b) by 537 days.

(21) Appl. No.: 10/646,171

(22) Filed: Aug. 22, 2003

(65) Prior Publication Data
US 2004/0121894 A1  Jun. 24, 2004

Related U.S. Application Data

(60) Provisional application No. 60/436,202, filed on Dec. 23, 2002.

(51) Int. Cl.
- B32B 18/00 (2006.01)
- A61C 13/00 (2006.01)
- A61C 8/00 (2006.01)
- C03C 3/076 (2006.01)

(52) U.S. Cl. ............ 428/699; 428/697; 428/702; 428/542.8; 433/212.1; 433/218; 433/222.1; 433/223; 501/57; 501/70; 501/59; 501/63; 501/72; 501/14

(58) Field of Classification Search ........ 428/697, 428/699, 702, 542.8; 433/212.1, 218, 222.1, 433/223; 501/57, 70, 59, 63, 72, 14; 106/35
See application file for complete search history.

(56) References Cited

U.S. PATENT DOCUMENTS

| | | | |
|---|---|---|---|
| 4,604,366 A | 8/1986 | Kacicz et al. | |
| 4,798,536 A | 1/1989 | Katz | |
| 5,653,791 A | 8/1997 | Panzera et al. | |
| 5,944,884 A | 8/1999 | Panzera et al. | |
| 6,120,591 A | 9/2000 | Brodkin et al. | |
| 6,155,830 A | 12/2000 | Brodkin et al. | |
| 6,428,614 B1 | 8/2002 | Brodkin et al. | |
| 6,527,846 B1 | 3/2003 | Beham | |
| 6,706,654 B2 * | 3/2004 | van der Zel .......... 501/32 |

FOREIGN PATENT DOCUMENTS

| EP | 0152338 A2 | 8/1985 |
|---|---|---|
| EP | 0690030 A1 | 1/1996 |
| EP | 1000 588 | 5/2000 |

(Continued)

OTHER PUBLICATIONS

PCT International Search Report with date of mailing Mar. 15, 2004.

(Continued)

Primary Examiner—Jennifer McNeil
Assistant Examiner—G. Blackwell
(74) Attorney, Agent, or Firm—Buchanan Ingersoll & Rooney PC (57) ABSTRACT

A pressable dental ceramic comprising a mixture of glass and glass-ceramic frits. A refractory filler is also combined with the frits. The dental ceramic contains an amount of leucite less than about 35 percent by weight. Other additives may be included such as pigments, opacifying agents and fluorescing agents. The dental ceramic comprises a cellular-like microstructure comprised of glassy regions surrounded by clusters of leucite crystals distributed around those glassy regions forming a cellular three-dimensional network.

50 Claims, 5 Drawing Sheets

FOREIGN PATENT DOCUMENTS

| | | |
|---|---|---|
| EP | 1000588 A2 | 5/2000 |
| EP | 1 245 548 | 10/2002 |
| EP | 1 253 116 | 10/2002 |
| EP | 1245548 A1 | 10/2002 |
| EP | 1253116 A1 | 10/2002 |
| EP | 1 329 430 | 7/2003 |
| EP | 1329430 A2 | 7/2003 |
| WO | WO 99-45889 | 9/1999 |
| WO | WO 99/45889 | 9/1999 |
| WO | WO 01/01925 A1 | 1/2001 |
| WO | WO 2004/060328 A1 | 7/2004 |

OTHER PUBLICATIONS

Hoeland W., et al: "Needle-like apatite-leucite glass-ceramic as a base material for the veneering of metal restorations in dentistry" Journal of Materials Science. Materials in Medicine, Chapman and Hall, London, GB, vol. 11, No. 1, Jan. 1, 2000, pp. 11-17.

PCT Written Opinion with date of mailing Oct. 5, 2004.

Fischer H., Weber M., Marx R., Lifetime Prediction of All-Ceramic Bridges by Computational Methods. J. Dent Res 82 (3):238-242, 2003.

* cited by examiner

PRESSABLE GLASS-CERAMICS WITH TEXTURED MICROSTRUCTURE

CROSS-REFERENCE TO RELATED APPLICATIONS

This application claims priority to U.S. Provisional Application No. 60/436,202, filed Dec. 23, 2002, which is incorporated herein by reference.

FIELD OF INVENTION

This invention relates generally to glass-ceramics comprising leucite and more specifically to glass-ceramics for use in the manufacture of dental restorations and methods of manufacture thereof.

BACKGROUND OF THE INVENTION

High-strength feldspathic dental porcelains were first introduced in the dental industry in the 1980s. Optec™ porcelain, the subject of U.S. Pat. No. 4,798,536, is one example of feldspathic porcelain that has been used in the manufacture of all-ceramic dental restorations. Currently, the most common technique for manufacturing all-ceramic dental restorations is heat-pressing, also known as injection molding, of all-ceramic cores. Dental glass-ceramic materials, such as OPC® pressable ceramic and Empress® pressable ceramic, exhibit flexure strength from about 120 MPa to about 180 MPa due to a relatively high fraction of leucite crystals embedded in the glass matrix. Historically, the first leucite-containing components of dental porcelains were produced by melting potassium feldspar with fluxes as described in U.S. Pat. No. 4,798,536, which is hereby incorporated by reference. Thus, these glass-ceramic materials are often also referred to as high-strength feldspathic dental porcelains or leucite-reinforced dental ceramics or glass-ceramics. The leucite content in these materials is higher than at least about 35 weight percent and most of the porcelains have a leucite content from about 45 to about 60 weight percent. As a result, they exhibit relatively high coefficients of thermal expansion (CTE) in excess of about $15 \times 10^{-6}/°$ C. (from room temperature to 500° C.) and require specifically developed porcelains with a matching high thermal expansion. At the same time, most of the porcelains used for porcelain-fused-to-metal (PFM) restorations have CTEs of about 12 to about $13 \times 10^{-6}/°$ C. (from room temperature to 500° C.) and are compatible with most commonly used precious and non-precious alloys having CTEs in the range of about 13 to about $15 \times 10^{-6}/°$ C. (from room temperature to 500° C.). Thus, these porcelains are commonly referred to as conventional porcelains.

One of the distinct advantages of the heat-pressing (injection molding) method for fabricating all-ceramic cores is exceptionally accurate and consistent margin adaptation. Only very few and the most experienced dental technicians can achieve the same accuracy building porcelain margins by hand. The most time-consuming procedure is manual fabrication of porcelain margins on multi-unit metal frameworks for fixed partial dentures (FPD) or bridges. To circumvent these difficulties, a new method commonly referred to as "pressing to metal" was recently introduced, where a heat-pressing technique is used to press high expansion leucite-based glass-ceramic directly onto a metal framework. As a result, to produce the finished restoration, the technique requires layering the press-to-metal core with the porcelain having a coefficient of thermal expansion exceeding that of conventional porcelains.

It would be extremely beneficial to have pressable all-ceramic cores compatible with these aforementioned porcelains and at the same time capable of being directly pressed to metal.

SUMMARY OF THE INVENTION

These and other objects and advantages are accomplished by the pressable dental ceramic of the present invention comprising a mixture of glass and glass-ceramic frits. A refractory filler is also combined with the frits. The dental ceramic contains an amount of leucite less than about 35 percent by weight. Other additives may be included such as pigments, opacifying agents and fluorescing agents. Prior to pressing, the dental ceramic comprises a cellular-like microstructure comprised of glassy regions surrounded by clusters of leucite crystals distributed around those glassy regions forming a cellular three-dimensional network and after pressing, the dental material comprises a textured microstructure.

In another embodiment, a pressable dental ceramic is formed by mixing and firing at least one glass frit and at least one glass-ceramic frit. Preferably, pellets or blanks are fabricated by mixing two frits, a relatively coarse glass frit and a very fine leucite-containing frit. Specifically, the average particle size of the leucite frit should be about six times smaller than the particle size of the glass frit. The pressable pellet exhibits a cellular-like microstructure comprised of glassy regions surrounded by clusters of leucite crystals distributed around those glassy regions forming a cellular three-dimensional network, which transforms into a textured microstructure upon pressing.

The pressable dental ceramics are useful for forming cores and frameworks for all ceramic dental restorations and as overlays for press-to-metal dental restorations including, but not limited to, orthodontic appliances, bridges, space maintainers, tooth replacement appliances, splints, crowns, partial crowns, dentures, posts, teeth, jackets, inlays, onlays, facing, veneers, facets, implants, abutments, cylinders, and connectors.

BRIEF DESCRIPTION OF THE DRAWINGS

Features of the present invention are disclosed in the accompanying drawings, wherein similar reference characters denote similar elements throughout the several views, and wherein.

DESCRIPTION OF THE INVENTION

Leucite-based glass ceramic materials of the present invention are made by a conventional heat-pressing technique, also known as injection molding, similar to procedures used to manufacture OPC® pressable ceramic available from Pentron Laboratory Technologies, LLC and Empress® pressable ceramic available from Ivoclar Corporation. In order to press cores for all-ceramic dental restorations using these conventional techniques and commercial equipment, the materials are formed into the shape of a blank or pellet. Blanks or pellets are fabricated by compacting and subsequently firing starting glass-ceramic powder comprising a mixture of various glass or glass-ceramic frits and additives such as pigments, opacifying agents and fluorescing agents. The essential feature of the present invention is that these blanks/pellets have a cellular-like microstructure comprised of glassy regions surrounded by clusters of leucite crystals distributed around those glassy regions forming a cellular three-dimensional network.

In one embodiment herein, a pressable dental ceramic pellet or blank is formed from a mixture of at least one glass frit, at least one glass-ceramic frit and at least one refractory filler. Preferably, the glass frit is present in an amount of from about 40 to about 65 percent by weight, the glass-ceramic frit is present in an amount of from about 35 to about 60 percent by weight and the refractory filler is present in an amount from about 0.5 to about 10 percent by weight. The glass-ceramic frit contains an amount of leucite of at least 60 percent by weight to provide an amount of leucite in the final dental ceramic composition of less than or equal to about 35 percent by weight. The refractory filler may comprise an amorphous silica in the form of a fused silica, fumed silica and mixtures thereof.

The role of the refractory filler is two-fold. It is needed to lower the thermal expansion of the porcelain and also to impart enough resistance to distortion to enable preserving accurate fit and marginal integrity during repetitive firing of the overlay porcelain onto the dental ceramic. Normally, the difference between the pressing temperature for a pressable core and the firing temperature of the overlay porcelain is at least 150° C. By contrast, in the invention herein, the difference between the pressing temperature for the pressable core and the firing temperature of the overlay porcelain is less than about 150° C. and preferably less than about 110° C. Materials of the present invention are pressable at temperatures as low as 980° C., but due to both their textured microstructure and the presence of the refractory filler, they can withstand the firing of the overlay porcelain thereon to temperatures as high as 900° C. (1652° F.), which is a small difference of 80° C.

The textured microstructure provides integrity to the dental ceramic and the refractory filler prevents distortion of the dental ceramic. In order to provide optimum results, the refractory filler should have a thermal expansion lower than the thermal expansion of the frits used in the pressable core material and a refractive index within about 0.2 of the refractive index of the frits. Opacifiers, such as zirconia, titania, zirconium silicate (ultrox) and tin oxide, which are conventional additives in dental ceramic and porcelain materials are different from the refractory fillers used herein because they are used to opacify the frits and must have a refractive index that is different from the refractive index of the frits by 0.5 or greater in order to opacify. Glass and glass ceramic frits have a refractive index in the range from about 1.45 to about 1.55, which is characteristic of most conventional alumo-silicate and alumo-boro-silicate glasses. The following Table 1 provides the refractive indices of various opacifers, glass and glass-ceramic frits and refractory fillers of the invention.

TABLE 1

Refractive Indices.

| Material | Crystal Structure | Refractive Index | Use | Difference In RI Between Frits And Material |
|---|---|---|---|---|
| TiO2 | Rutile | 2.7 | Opacifier | 1.2 |
| ZrO2 | Mg-Stabilized Zirconia (Cubic And Tetragonal) | 2.15 | Opacifier | 0.65 |
| SnO2 | Casseterite | 2.093 | Opacifier | 0.593 |
| ZrSiO4 | | 1.95 | Opacifier | 0.45 |
| Al2O3 | Corundum | 1.76 | Opacifier | 0.26 |
| ZnO | | 2.01 | Opacifier | 0.51 |
| Glass and Glass-Ceramic Frits | | 1.45-1.55 | | 0 |
| leucite | | 1.5 | | 0 |
| Cordierite | | 1.53 | Refractory Filler | 0.03 |
| Mullite | | 1.64 | Refractory Filler | 0.14 |
| Spinel | | 1.72 | Refractory Filler | 0.22 |
| Alumina | | 1.76 | Can Be Used As Refractory Filler Only In Combination With Others | 0.26 |
| Fused (amorphous) silica | | 1.46 | Refractory Filler | 0.04 |
| Quartz (crystalline silica) | | 1.55 | Refractory Filler | 0.05 |

Figure 1:
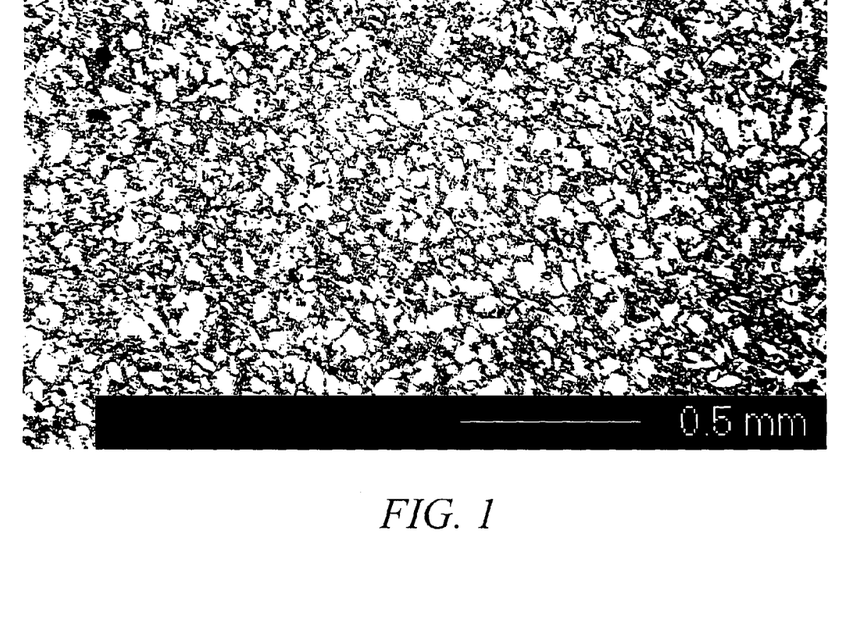
FIG. 1 is a photomicrograph of the dental ceramic prior to pressing.
Figure 2:
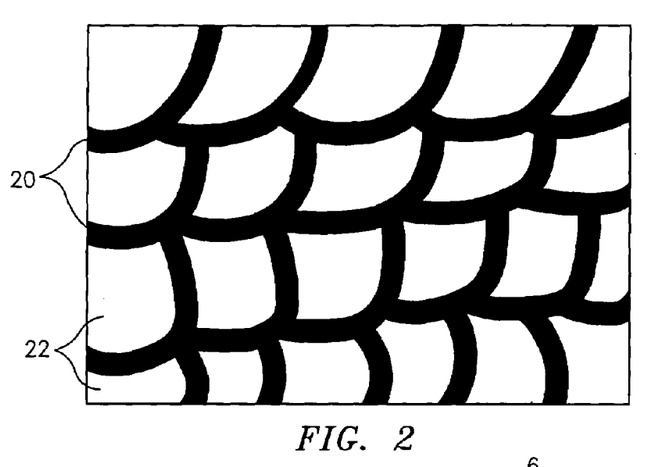
FIG. 2 is a schematic diagram of the photomicrograph of FIG. 1.
Figure 7:
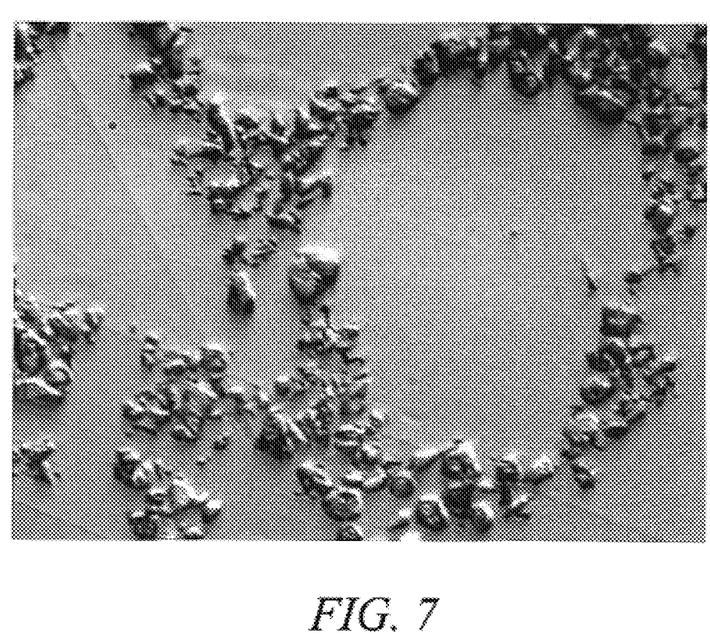
FIG. 7 shows a magnified section of an area in the photomicrograph of FIG. 1.

Prior to pressing the dental ceramic blank or pellet into a dental restorative material, the dental ceramic comprises a cellular-like microstructure comprised of glassy regions surrounded by clusters of leucite crystals distributed around those glassy regions forming a cellular three-dimensional network. FIGS. 1, 2 and 7 clearly represent this aspect of the dental ceramic.

In yet another embodiment, at least one glass frit is mixed with at least one glass-ceramic frit and sintered to form a pressable dental ceramic. Preferably, pellets are fabricated by mixing two frits, a relatively coarse glass frit and a very fine leucite-containing frit. Opacifying agents, fluorescing agents, other additives and pigments may be added to the mixture as well. The particle size distribution of the component frits are engineered specifically to ensure that during the blending of the frits and compacting the resulting mixture into the shape of pellets, the leucite frit will be coordinated into interstitial sites between much larger particles of the glass frit. Specifically, the average particle size of the leucite frit should be about six times smaller than that of the glass frit. More specifically, the average particle size (mv) of the leucite frit should be less than about 7 microns (mµ) and the average particle size (mv) of the glass frit should be more than about 35 mµ. It is most preferred that the leucite frit has an mv $\leq 6$ mµ and the glass frit has an mv $\geq 36$ mµ.

The pressing temperature of the dental ceramics discussed herein is from about 980 to about 1030° C. After pressing the dental ceramic into a mold whereby it is formed into the desired shape, it is able to withstand firing of a porcelain thereon at a range from about 830 to about 900° C. without distorting the dental ceramic.

FIG. 1 represents a micrograph of the microstructure of a pellet (from Example 1 below) manufactured in accordance herein comprising a three-dimensional network of leucite arranged in a cellular pattern and FIG. 2 shows a schematic diagram of the micrograph of FIG. 1. FIG. 2 depicts leucite-containing sections 20 separated by glassy, leucite-free sections 22. During pressing, the roughly equiaxed "cells" of the cellular microstructure are being stretched in the direction of viscous flow and flattened in the direction normal to the flow which results in a so-called "pancake" structure as shown in FIGS. 3 and 4.

Figure 3:
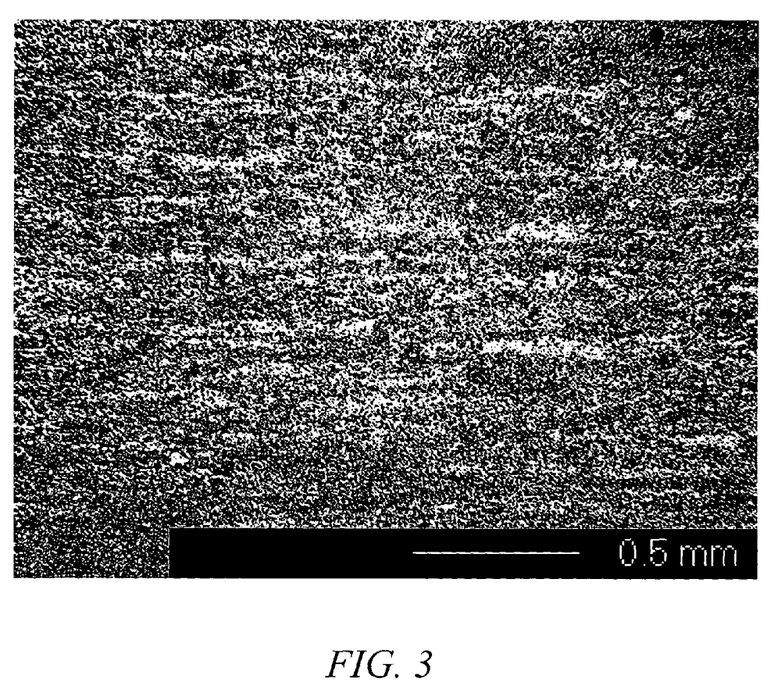
FIG. 3 is a photomicrograph of the dental ceramic of FIG. 1 after pressing.
Figure 4:
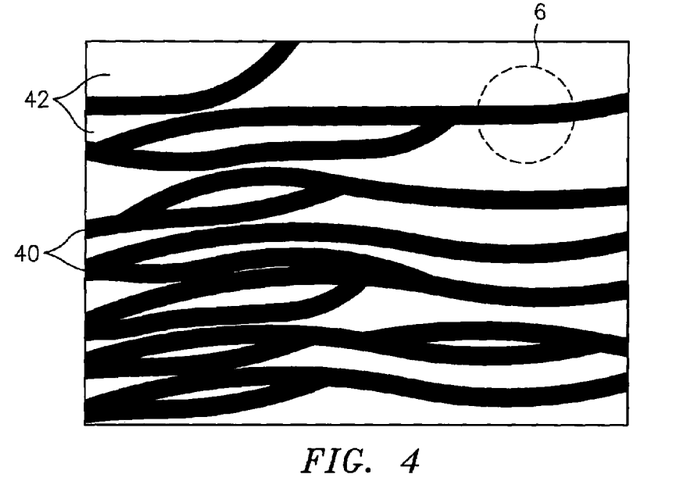
FIG. 4 is a schematic diagram of the photomicrograph of FIG. 3.

FIG. 3 is a micrograph of the pellet from FIG. 1 that has been pressed at 1020° C. and FIG. 4 is a schematic diagram of the micrograph of FIG. 3. FIG. 4 shows leucite-containing layers 40 separated by glassy, leucite-free layers 42. This "pancake" structure is well known in metallurgy as a type of structure formed by cold-working of metals. In the case of metals this "pancake" microstructure is formed by plastic deformation of the originally equiaxed grains and results in a stronger metal, an effect known as strain-hardening. In the glass-ceramic material of the present invention, somewhat similar microstructural changes resulting in a pancake appearance of the microstructural features (cells) are achieved by constrained viscous flow of the glass-ceramic material forced through narrow channels of the refractory mold.

This coordination between particle sizes of the component frits results in a cellular microstructure (as shown in FIGS. 1 and 2) in the pellet, which upon pressing transforms into a "pancake" or layered type of microstructure (as shown in FIGS. 3 and 4). The inventor herein has found that this combination produces surprisingly high strength and, at the same time, relatively low expansion. In the following description, the term "layered" is used interchangeably with the term "textured" to describe the generic type of microstructure associated with the materials described herein.

Figure 6:
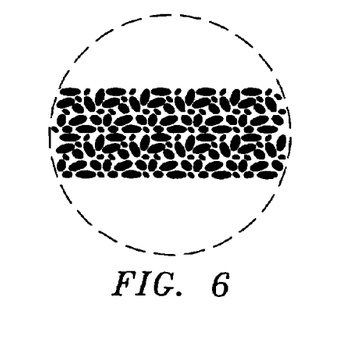
FIG. 6 shows an enlarged view of a section of the schematic diagram shown in FIG. 4.

FIG. 6 shows an enlarged section of individual leucite crystals from FIG. 4. The schematic diagram shown in FIG. 2 would render the same depiction of individual leucite crystals as shown in FIG. 6. FIG. 7 shows a magnified section of an area in the dental ceramic shown in FIG. 1. It shows individual leucite crystals that are schematically shown in FIG. 6.

The following examples illustrate the invention.

EXAMPLE 1 AND COMPARATIVE EXAMPLE 2

To illustrate the concept of the textured microstructure, two examples were carried out having the same composition, but with different particle sizes. Two frits with compositions and properties given in Table 2 below were mixed with a small amount of an opacifier and hand-pressed into cylindrical pellets. A first glass frit (a low expansion frit) with a CTE of about $9 \times 10^{-6}/°$ C. (from room temperature to 500° C.) was added as approximately 57 wt % of the mixture. A second, high expansion frit, containing about 60% to about 70% of leucite with a CTE of about $18 \times 10^{-6}/°$ C. (from room temperature to 500° C.) was added as approximately 40% of the mixture. Additionally, about 3 wt % of $Al_2O_3$ was added as a refractory filler (alumina is used for the sake of illustration of the concept since it has refractive index that is a bit too high to use in substantial quantity without over opacifying the material). The high expansion frit was fabricated in two particle size variations, fine with average particle size of about 6 mµ and coarse with average particle size of about 18 mµ. The fine frit was used in Example 1 and the coarse frit was used in comparative Example 2. The same glass frit with an average particle size of about 33 mµ was used in both examples. Component frits and alumina were mixed and dry-pressed into small cylindrical pellets weighing approximately 2 grams each. Pellets of Example 1 and Example 2 were fired in vacuum to full density using the same firing cycle. Various dental articles as well as rods for 3-pt bending were pressed into refractory molds made from Universal™ Investment material using a conventional pressing technique in the AutoPress® Plus pressing furnace (available from Pentron Laboratory Technologies, LLC) at 1020° C. Rods were tested in 3-pt bending equipment. The material of Example 1 with the layered pancake microstructure exhibited a flexure strength of 137±12 MPa and the material from comparative Example 2 having an equiaxed microstructure exhibited a flexure strength of 92±5 MPa.

TABLE 2

Component frit compositions and properties

|  | Glass Frit | Leucite Frit | Overall Composition of Example 1 and Comparative Example 2 |
|---|---|---|---|
| CTE @ 500° C., ppm = $10^{-6}$ (° C.)$^{-1}$ | 9 | 18 | 13.3 |
| Glass Transition Temperature | 600 | 650 | 610 |
| Average particle size, µm | 33 | 6 (Example 1) 18 (Example 2) |  |
| SiO2 | 67.93 | 65.01 | 64.69 |

TABLE 2-continued

Component frit compositions and properties

|  | Glass Frit | Leucite Frit | Overall Composition of Example 1 and Comparative Example 2 |
|---|---|---|---|
| B2O3 | 0.00 | 0.00 | 0 |
| Al2O3 | 13.35 | 18.01 | 17.79 |
| ZnO | 0.00 | 0.00 | 0 |
| CaO | 1.99 | 0.77 | 1.44 |
| MgO | 0.00 | 0.00 | 0 |
| BaO | 0.00 | 0.00 | 0 |
| Li2O | 0.00 | 0.51 | 0.2 |
| K2O | 10.16 | 13.89 | 11.34 |
| Na2O | 6.18 | 1.81 | 4.24 |
| TiO2 | 0.00 | 0.00 | 0 |
| ZrO2 | 0.00 | 0.00 | 0 |
| CeO2 | 0.40 | 0.00 | 0.28 |

EXAMPLE 3

The same glass as the one used in Examples 1 and 2 in Table 2 above was milled to yield a glass (a low expansion) frit with an average particle size of 36 μm. The high expansion frit of Examples 1 and 2 was combined with a second high expansion frit in the weight ratio of from 1:1 to 1:1.5. Both high expansion frits had a particle size of about 6 μm. The mixture of the two high expansion frits was combined with the glass frit in the ratio of about 1:1. Additionally, about 2 wt % of $Al_2O_3$ and about 2 wt % of fused silica were added to lower the thermal expansion of the mixture of the frits and to impart sufficient resistance to distortion to enable firing of the overlay porcelain at temperatures up to about 890° C.

Overall composition of Example 3 and Example 1 & 2 from above.

|  |  |  | Frits Used in Example 3 | | |
|---|---|---|---|---|---|
| Overall composition, wt % | Examples 1 & 2 | Example 3 | Glass Frit | First Leucite Frit | Second Leucite Frit |
| SiO2 | 64.69 | 65.37 | 67.39 | 65.01 | 63.82 |
| B2O3 | 0.00 | 0.00 | 0.00 | 0.00 | 0.00 |
| Al2O3 | 17.79 | 17.03 | 13.35 | 18.01 | 17.69 |
| ZnO | 0.00 | 0.00 | 0.00 | 0.00 | 0.00 |
| CaO | 1.44 | 1.30 | 1.99 | 0.77 | 0.76 |
| MgO | 0.00 | 0.00 | 0.00 | 0.00 | 0.00 |
| BaO | 0.00 | 0.00 | 0.00 | 0.00 | 0.00 |
| Li2O | 0.20 | 0.67 | 0.00 | 0.51 | 1.88 |
| K2O | 11.34 | 11.54 | 10.16 | 13.89 | 13.67 |
| Na2O | 4.24 | 3.74 | 6.18 | 1.81 | 1.77 |
| TiO2 | 0.00 | 0.00 | 0.00 | 0.00 | 0.00 |
| ZrO2 | 0.00 | 0.00 | 0.00 | 0.00 | 0.00 |
| CeO2 | 0.28 | 0.35 | 0.40 | 0.00 | 0.41 |

Figure 5:
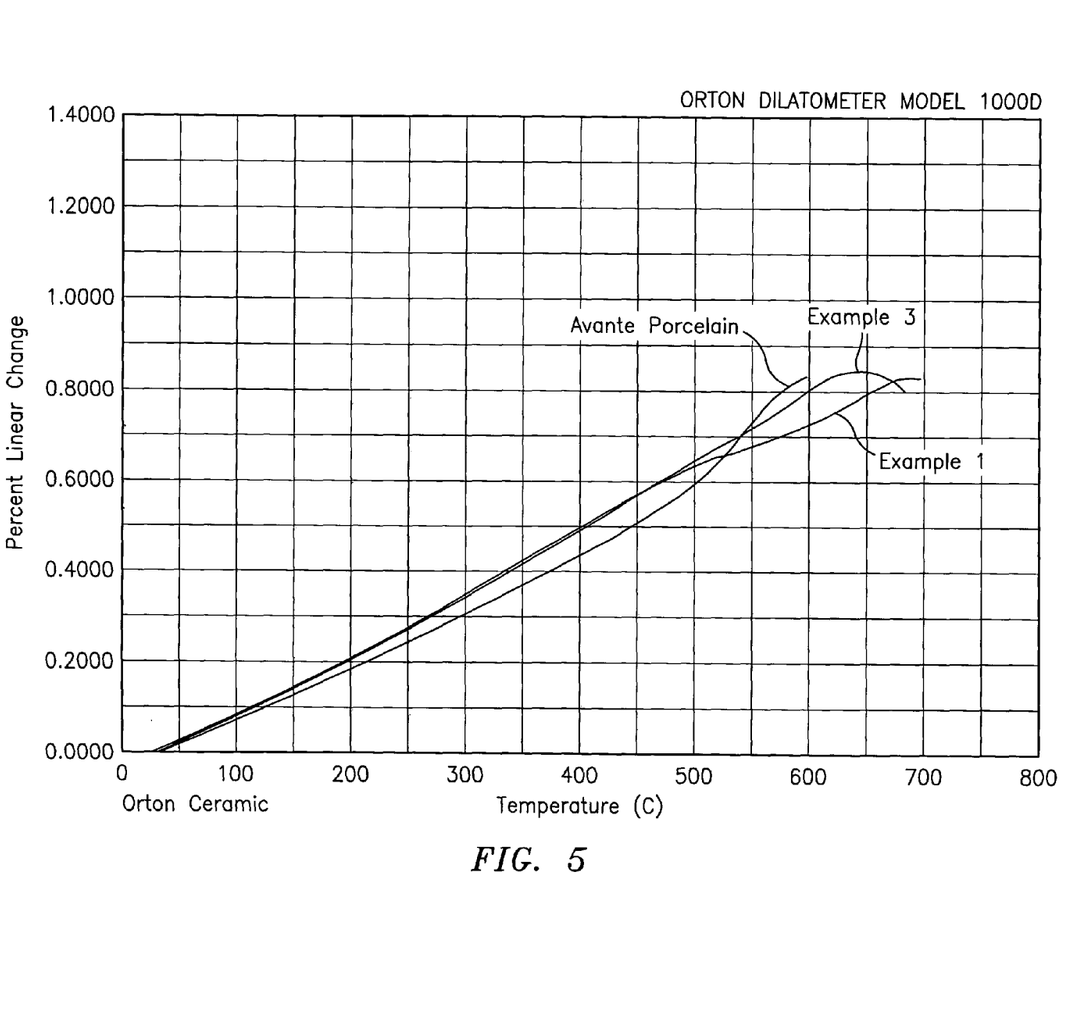
FIG. 5 shows thermal expansion curves for three different materials.

Pellets were fabricated as described in Examples 1 and 2 above. Heat-pressing was carried out at 990° C. using the same equipment and procedures as in the previous examples. A plastic rod with a length of 63 mm was invested in a 300 g investment ring. Following burn-out, pressing and divesting, the as-pressed rod was cut to 51 mm and used to measure thermal expansion from room temperature to 700° C. The CTE was measured as $13.6 \times 10^{-6}/°$ C. and $14.0 \times 10^{-6}/°$ C. (from room temperature to 500° C. and to 600° C., respectively), and the GTT was 570° C.±20° C. measured at as-pressed condition. FIG. 5 shows thermal expansion curves of the pressed glass-ceramics of Examples 1 and 3 overlaid with thermal expansion curves of Avante Micro Crystal® body and incisal porcelain. Some of the pressed samples were sectioned, mounted, polished and etched for microscopic examination to confirm the presence of a textured microstructure as shown in FIGS. 3 and 4.

EXAMPLE 4

Strength, Weibull Modulus And Compatibility With Porcelain-Fused-To-Metal (PFM) Porcelain A mixture of frits used in Example 3 and fused silica was shaded by using about 1% of commercially available pigments. Pellets were fabricated as described above in the previous examples. Various dental articles and various test specimens including 24 rods for a 3-pt bend test were pressed at 1000° C. using the equipment and procedures described above. Following normal divesting procedures, as-pressed rods of about 20 mm in length and about 3.3 mm in diameter were loaded to failure in three-point bending configuration. Three-point flexure strength was determined to be 142 MPa with a standard deviation as low as 12 MPa (8.4%). In addition, the measured strength values were ranked and used to calculate the Weibull modulus (m). An extremely high Weibull modulus of 13.6 and a Weibull strength value ($\sigma_0$) of 146.9 MPa with the correlation factor ($R^2$) of 0.95 were established for this material. Based on the determined Weibull parameters, a stress value corresponding to the survival probability of 99.9%, ($\sigma_{99.9\%}$) (representing the case when only one specimen in 1000 fails) was calculated to be 88.5 MPa. Both values for Weibull modulus (m), and $\sigma_{99.9\%}$ were surprisingly high compared to values for leucite-containing, lithium disilicate and glass infiltrated dental ceramics known from the literature (H. Fisher, M. Weber, and R. Marx, Lifetime Prediction of All-ceramic Bridges by Computational Methods, *J Dent Res* 82 (3): 238-242, 2003) which is hereby incorporated by reference and which results are summarized in Table 4 below. Most important, the $\sigma_{99.9\%}$ of 88.5 MPa was substantially higher than the maximum principal stress of 72 MPa associated with peak loads produced during the normal masticating process. This data indicates the specific benefits associated with a type of microstructure, termed layered or textured, characteristic for glass-ceramic materials of this invention. The leucite-based glass-ceramics of this invention having leucite content of less than 35% still exhibits strength comparable to leucite-reinforced dental ceramics such as Empress® and OPC® which have higher leucite content. At the same time, in reliability, it matches much stronger and tougher ceramic materials such as some lithium disilicate and glass infiltrated ceramics (see Fisher et al. for m values for these materials).

TABLE 4

Data from Fisher Article and from Example 3 herein.

| Material | Type of Glass-Ceramic | Elastic Modulus GPa | Poisson's Ration v | $\sigma_0$ MPa | Weibull Modulus m | Calculated $\sigma_{99.9\%}$ | $\sigma_{1,\,max}$ MPa @ 600 N load | Reliability Factor = $\sigma_{99.9\%}/\sigma_1$ |
|---|---|---|---|---|---|---|---|---|
| Empress ® 1* | leucite | 67 | 0.19 | 89 | 8.6 | 40 | 72 | 0.55 |
| Empress ® 2* | lithium-disilicate | 96 | 0.22 | 289 | 8.8 | 132 | 85 | 1.55 |
| InCeram ™ Alumina** | glass-infiltrated | 251 | 0.22 | 290 | 4.6 | 65 | 130 | 0.50 |
| 3Y-SZ ™*** | YTZP zirconia | 205 | 0.31 | 937 | 18.4 | 644 | 125 | 5.15 |
| Example 3 | leucite | 70 | 0.2 | 146.9 | 13.6 | 88 | 72 | 1.23 |

*IVOCLAR AG CORPORATION
**VITA ZAHNFABRIK H. RAUTER GMBH & CO.
***METOXIT AG

A number copings and nearly full contour crowns were pressed at temperatures of varying from 980° C. to 1000° C. to evaluate fit and absence of distortion from both white (unshaded) and shaded material. The pressed copings were layered with Avante Microcrystal® porcelain (Pentron) and d.SIGN® porcelain (Ivoclar). Both porcelains are currently used to fabricate PFM restorations using alloys with a CTE of about 13-15×10⁻⁶/° C. Porcelains were fired at temperatures of varying from 830° C. to 900° C. with grinding and the addition of new porcelain for up to four times. No distortion, cracking, crazing or discoloration was observed.

A standard master die was used to design a standard framework for a 4-unit posterior bridge with up to 4 mm long margins. This standard framework was duplicated in a variety of metals including Rexillium III®, Rexillium®V, REX 4®, REX CC® and Avante MicroFine™ 50, 60, 68, 76 alloys and Rx G-Universal. Following application of two coats of Avante® Opaque these frameworks were invested in 300 g rings often together with wax-ups for all-ceramic single units. Shaded pellets of the glass-ceramic composition of Example 3 were pressed at 1000° C. Following standard divesting and cleaning procedures the press-to-metal bridges were layered with Avante Microcrystal® and d.SIGN® porcelains and fired with grinding and addition of new porcelain for up to four times. No distortion, cracking, crazing or discoloration was observed.

The essential feature of the glass-ceramic material of this invention is its engineered microstructure that results in a relatively high strength at low leucite content and therefore a relatively low CTE in the range of 12.5-14.5 ppm. As a result, all-ceramic cores made from this material are compatible with some porcelains used in PFM restorations fabricated on a wide range of popular and commonly used alloys having a CTE in the range of 13-15 ppm. The material of the present invention can be pressed onto metal directly.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A dental ceramic comprising: a glass frit; a glass-ceramic frit comprising leucite; and a refractory filler having a thermal expansion lower than the thermal expansion of the frits and a refractive index within ±0.2 of the refractive index of the frits; wherein leucite is present in the dental ceramic in an amount less than about 35% by weight; wherein the thermal expansion of the dental ceramic is in the range of about 12.5×10⁻⁶/° C. to about 14.5×10⁻⁶/° C. measured from room temperature to 500° C.; wherein the dental ceramic is pressable from about 980 to about 1030° C.; and wherein the dental ceramic can withstand firing of a porcelain onto the dental ceramic without distortion of the dental ceramic at a range from about 830° C. to about 900° C.

2. The dental ceramic of claim 1 wherein the refractive index of the glass and glass-ceramic frits and the refractive index of the refractory filler are substantially the same or within about ±0.2 of one another.

3. The dental ceramic of claim 1 wherein the glass frit has a glass transition temperature ≧580° C.

4. The dental ceramic of claim 1 wherein the glass-ceramic frit has a glass transition temperature ≧600° C.

5. The dental ceramic of claim 1 wherein the glass frit has an average particle size equal to or greater than about six times the average particle size of the glass-ceramic frit.

6. The dental ceramic of claim 1 wherein the glass frit has an average particle size of equal to or greater than about 35 microns and the glass-ceramic frit has an average particle size of equal to or less than about 6 microns.

7. The dental ceramic of claim 1 further comprising a second glass-ceramic frit.

8. The dental ceramic of claim 1 having a three-point bend strength measured per ISO 6872 standard equal to higher than 130 MPa.

9. The dental ceramic of claim 1 having a three-point bend strength measured per ISO 9693 standard equal to higher than 130 MPa.

10. The dental ceramic of claim 1 further comprising one or more of a pigment, opacifying agent and fluorescing agent.

11. The dental ceramic of claim 1 wherein the glass frit is present in an amount from about 40 to about 65 percent by weight, the glass-ceramic frit is present in an amount from about 35 to about 60 percent by weight and the refractory filler is present in an amount from about 0.5 to about 10 percent by weight.

12. The dental ceramic of claim 1, wherein the frits have a refractive index of about 1.45 to about 1.55.

13. The dental ceramic of claim 1, having a composition that is essentially free of lithium.

14. The dental ceramic of claim 1 wherein the refractory filler is selected from the group consisting of silica, cordierite, mullite, alumina, spinel, and mixtures thereof.

15. The dental ceramic of claim 14 wherein the silica is amorphous silica and is selected from the group consisting of fused silica, fumed silica and mixtures thereof.

16. The dental ceramic of claim 1 in combination with a porcelain overlay having a maturing temperature higher than about 830° C.

17. The dental restoration of claim 16 selected from the group consisting of orthodontic appliances, overlays, bridges, space maintainers, tooth replacement appliances, splints, crowns, partial crowns, dentures, posts, teeth, jackets, inlays, onlays, facing, veneers, facets, implants, abutments, cylinders, and connector.

18. The dental ceramic of claim 1 wherein the dental ceramic can withstand firing of a porcelain onto the dental ceramic without distortion of the dental ceramic at a range from about 830 to about 900° C.; the dental ceramic in combination with a porcelain overlay having a maturing temperature higher than about 830° C.; wherein the difference between the pressing temperature of the dental ceramic and the firing temperature of the overlay is less than 150° C.

19. The dental restoration of claim 18 selected from the group consisting of orthodontic appliances, overlays, bridges, space maintainers, tooth replacement appliances, splints, crowns, partial crowns, dentures, posts, teeth, jackets, inlays, onlays, facing, veneers, facets, implants, abutments, cylinders, and connector.

20. The dental ceramic of claim 1, wherein the dental ceramic can withstand firing of a porcelain onto the dental ceramic without distortion of the dental ceramic at a range from about 830 to about 900° C.; in combination with a porcelain overlay on the dental ceramic having a maturing temperature higher than about 830° C., and a metal framework.

21. The dental restoration of claim 20 selected from the group consisting of orthodontic appliances, overlays, bridges, space maintainers, tooth replacement appliances, splints, crowns, partial crowns, dentures, posts, teeth, jackets, inlays, onlays, facing, veneers, facets, implants, abutments, cylinders, and connector.

22. The dental ceramic of claim 1 having a cellular-like microstructure in a prior to pressing and a layered microstructure comprising leucite-rich layers separated by glass-rich layers after pressing.

23. The dental ceramic of claim 22 wherein the leucite-rich layers and glass-rich layers are oriented normal to a direction of mastication loads in a person's mouth.

24. The dental restoration of claim 23 selected from the group consisting of orthodontic appliances, overlays, bridges, space maintainers, tooth replacement appliances, splints, crowns, partial crowns, dentures, posts, teeth, jackets, inlays, onlays, facing, veneers, facets, implants, abutments, cylinders, and connector.

25. A dental ceramic comprising: a glass frit; a glass-ceramic frit comprising leucite; and a refractory filler; wherein the glass frit has an average particle size equal to or greater than about six times the average particle size of the glass-ceramic frit.

26. The dental ceramic of claim 25 wherein the glass frit is present in an amount from about 40 to about 65 percent by weight, the glass-ceramic frit is present in an amount from about 35 to about 60 percent by weight and the refractory filler is present in an amount from about 0.5 to about 10 percent by weight.

27. The dental ceramic of claim 25 wherein the glass frit has an average particle size of equal to or greater than about 35 microns and the glass-ceramic frit has an average particle size of equal to or less than about 6 microns.

28. The dental ceramic of claim 25 having a cellular microstructure prior to pressing and a textured microstructure after pressing.

29. The dental ceramic of claim 25 having a three-point bend strength measured per ISO 6872 standard equal to higher than 130 MPa.

30. The dental ceramic of claim 25 having a three-point bend strength measured per ISO 9693 standard equal to higher than 130 MPa.

31. The dental ceramic of claim 25 wherein the leucite content of the dental ceramic is less than 35 percent by weight.

32. The dental ceramic of claim 25 wherein the dental ceramic is pressable from about 980 to about 1030° C., and wherein the dental ceramic can withstand firing of a porcelain onto the dental ceramic without distortion of the dental ceramic at a range from about 830 to about 900° C.

33. The dental restoration of claim 25 selected from the group consisting of orthodontic appliances, overlays, bridges, space maintainers, tooth replacement appliances, splints, crowns, partial crowns, dentures, posts, teeth, jackets, inlays, onlays, facing, veneers, facets, implants, abutments, cylinders, and connector.

34. The dental ceramic of claim 25, in combination with a porcelain overlay having a maturing temperature higher than about 830° C.

35. The dental ceramic of claim 34 having a textured microstructure.

36. The dental restoration of claim 34 selected from the group consisting of orthodontic appliances, overlays, bridges, space maintainers, tooth replacement appliances, splints, crowns, partial crowns, dentures, posts, teeth, jackets, inlays, onlays, facing, veneers, facets, implants, abutments, cylinders, and connector.

37. The dental ceramic of claim 25, in combination with a porcelain overlay on the dental ceramic having a maturing temperature higher than about 830° C., and a metal framework.

38. The dental restoration of claim 37 selected from the group consisting of orthodontic appliances, overlays, bridges, space maintainers, tooth replacement appliances, splints, crowns, partial crowns, dentures, posts, teeth, jackets, inlays, onlays, facing, veneers, facets, implants, abutments, cylinders, and connector.

39. The dental ceramic of claim 25, having a composition that is essentially free of lithium.

40. A method of making a dental restoration comprising: heating a ceramic pellet or blank to a temperature in the range from about 980° C. to about 1030° C. and pressing the ceramic pellet or blank, wherein the ceramic pellet or blank comprises a dental ceramic comprising a glass frit, a glass-ceramic frit comprising leucite, and a refractory filler having a thermal expansion lower than the thermal expansion of the frits and a refractive index within ±0.2 of the refractive index of the frits, wherein leucite is present in the dental ceramic in an amount less than about 35% by weight, and wherein the thermal expansion of the dental ceramic is in the range of about 12.5×10⁻⁶/° C. to about 14.5×10⁻⁶/° C. measured from room temperature to 500° C., into a mold space that has been placed in a pressing furnace, whereby the ceramic pellet conforms to the mold space to form a ceramic core; removing the ceramic core from the mold space; applying and shaping a dental porcelain powder onto the ceramic core; and heating the shaped dental porcelain powder to a temperature in the range from about between about 830° C. to about 900° C. to fuse the dental porcelain powder to the ceramic core.

41. The method of claim 40 wherein the porcelain has a coefficient of thermal in the range of about $12.0 \times 10^{-6}$/° C. to about $14.0 \times 10^{-6}$/° C. in the temperature range of 25° C. to 500° C.

42. A method of making a dental restoration comprising: forming a metal framework; heating a ceramic pellet or blank to a temperature in the range from about 980° C. to about 1030° C. and pressing the ceramic pellet or blank, wherein the ceramic pellet or blank comprises a dental ceramic comprising a glass frit, a glass-ceramic frit comprising leucite, and a refractory filler having a thermal expansion lower than the thermal expansion of the frits and a refractive index within ±0.2 of the refractive index of the frits, wherein leucite is present in the dental ceramic in an amount less than about 35% by weight, and wherein the thermal expansion of the dental ceramic is in the range of about $12.5 \times 10^{-6}$° C. to about $14.5 \times 10^{-6}$/° C. measured from room temperature to 500° C., onto the metal framework to from a ceramic overlay; applying and shaping a dental porcelain powder onto the ceramic overlay; and heating the shaped dental porcelain powder to between about 830° C. to about 900° C. to fuse the dental porcelain powder to the ceramic core.

43. The method of claim 42 wherein the metal framework comprises a precious, semiprecious or non-precious alloy.

44. The method of claim 42 wherein metal framework is produced by casting, powder metallurgy or rapid prototyping techniques.

45. The method of claim 44 wherein the casting comprises capillary casting.

46. A method of making a dental restoration comprising: heating a ceramic pellet or blank to a temperature in the range from about 980° C. to about 1030° C. and pressing the ceramic pellet or blank, wherein the ceramic pellet or blank comprises a dental ceramic comprising a glass frit, a glass-ceramic frit comprising leucite, and a refractory filler having a thermal expansion lower than the thermal expansion of the frits and a refractive index within ±0.2 of the refractive index of the frits, wherein leucite is present in the dental ceramic in an amount less than or equal to about 35% by weight, wherein the thermal expansion of the dental ceramic is in the range of about 12.5 to about 14.5 measured from room temperature to 500° C. whereby the ceramic pellet conforms to the mold space to form a ceramic core; removing the ceramic core from the mold space; applying and shaping a dental porcelain powder onto the ceramic core; and heating the shaped dental porcelain powder to a temperature in the range from about between about 830° C. to about 900° C. to fuse the dental porcelain powder to the ceramic core.

47. A method of making a dental restoration comprising: forming a metal framework; heating a ceramic pellet or blank to a temperature in the range from about 980° C. to about 1030° C. and pressing the ceramic pellet or blank, wherein the ceramic pellet or blank comprises a dental ceramic comprising a glass frit, a glass-ceramic frit comprising leucite, and a refractory filler having a thermal expansion lower than the thermal expansion of the frits and a refractive index within ±0.2 of the refractive index of the frits, wherein leucite is present in the dental ceramic in an amount less than or equal to about 35% by weight, wherein the thermal expansion of the dental ceramic is in the range of about 12.5 to about 14.5 measured from room temperature to 500° C. onto the metal framework to from a ceramic overlay; applying and shaping a dental porcelain powder onto the ceramic overlay; and heating the shaped dental porcelain powder to between about 830° C. to about 900° C. to fuse the dental porcelain powder to the ceramic core.

48. The method of claim 47 wherein the metal framework comprises a precious, semiprecious or non-precious alloy.

49. The method of claim 47 wherein metal framework is produced by casting, powder metallurgy or rapid prototyping techniques.

50. The method of claim 49 wherein the casting comprises capillary casting.

* * * * *

UNITED STATES PATENT AND TRADEMARK OFFICE
CERTIFICATE OF CORRECTION

| | |
|---|---|
| PATENT NO. | : 7,279,238 B2 |
| APPLICATION NO. | : 10/646171 |
| DATED | : October 9, 2007 |
| INVENTOR(S) | : Dmitri Brodkin |

It is certified that error appears in the above-identified patent and that said Letters Patent is hereby corrected as shown below:

Please correct the typographical errors as follows:

Col. 13, Claim 42, line 29, please delete "from" and insert --form--

Col. 14, Claim 47, line 31, please delete "from" and insert --form--

Signed and Sealed this

Twenty-seventh Day of May, 2008

JON W. DUDAS
*Director of the United States Patent and Trademark Office*